United States Patent [19]

Watson et al.

[11] Patent Number: 5,098,411
[45] Date of Patent: Mar. 24, 1992

[54] CLOSED END HOLLOW STYLET ASSEMBLY

[75] Inventors: David A. Watson, Goleta; Gary P. East, Santa Barbara, both of Calif.

[73] Assignee: Pudenz-Schulte Medical Research Corporation, Goleta, Calif.

[21] Appl. No.: 712,689

[22] Filed: Jun. 10, 1991

[51] Int. Cl.$^5$ .............................................. A61M 25/00
[52] U.S. Cl. ...................................... 604/268; 604/274
[58] Field of Search ............... 604/268, 272, 274, 239, 604/280, 283

[56] References Cited

U.S. PATENT DOCUMENTS

| | | |
|---|---|---|
| 3,136,316 | 6/1964 | Beall .................. 604/268 X |
| 3,516,410 | 6/1970 | Hakim ................... 604/268 |
| 3,890,970 | 6/1975 | Gullen . |
| 4,610,671 | 9/1986 | Luther . |
| 4,710,180 | 12/1987 | Johnson ............... 604/274 X |
| 4,790,830 | 12/1988 | Hamacher ............. 604/274 |
| 4,950,232 | 8/1990 | Ruzicka et al. . |
| 4,961,729 | 10/1990 | Vaillancourt . |

FOREIGN PATENT DOCUMENTS 277127  5/1934  Italy ..................... 604/272

Primary Examiner—John D. Yasko
Attorney, Agent, or Firm—Kelly, Bauersfeld & Lowry

[57] ABSTRACT

A stylet assembly is provided for inserting a catheter into a brain ventricle and providing a cerebrospinal fluid flashback indicia of proper catheter positioning. The stylet assembly includes an elongated, generally cylindrical rigid hollow stylet having an open distal end, a rounded blunt proximal end, and an internal fluid passageway extending the length of the stylet. A relatively large single aperture is provided through the stylet adjacent to its proximal end, for permitting fluid flow into the internal fluid passageway. The aperture is configured to underlie a plurality of catheter inlet apertures and has a width generally corresponding with the diameter of the internal fluid passageway. An elastomeric hub surrounds a portion of the stylet adjacent to the distal end. The hub is configured to permit the flow of cerebrospinal fluid through the open distal end, and allows the open distal end of the stylet to be selectively manually occluded with a finger to prevent the flow of cerebrospinal fluid therethrough.

12 Claims, 1 Drawing Sheet

CLOSED END HOLLOW STYLET ASSEMBLY

BACKGROUND OF THE INVENTION

This invention relates generally to surgically implanted shunt systems utilized to drain cerebrospinal fluid from a brain ventricle. More particularly, the present invention relates to stylets utilized to introduce ventricular catheters utilized in cerebrospinal fluid shunt systems.

As is well known in the medical arts, to relieve undesirable accumulation of fluids it is frequently necessary to provide a means for draining a fluid from one part of the human body to another in a controlled manner. This is required, for example, in the treatment of hydrocephalus, an ailment usually afflicting infants or children in which fluids which ought to drain away instead accumulate within the skull and thereby exert extreme pressure and skull deforming forces.

In treating hydrocephalus, cerebrospinal fluid accumulated in the brain ventricles is drained away by a catheter inserted into a ventricle through the skull, and the catheter is connected to a tube which conducts the fluid away from the brain to be reintroduced into the vascular system, as by extending through the patient's jugular vein to the atrium portion of the heart. To control the flow of cerebrospinal fluid and maintain the proper pressure in the brain ventricle, a pump or valve is placed in the conduit between the brain and the heart. The brain ventricles are normally large enough to easily accommodate the end of a catheter several millimeters in diameter. Such ventricular catheters are commonly provided with small holes through their walls for receiving cerebrospinal fluid from the ventricle. To insert the ventricular catheter, a hole is bored through the skull, and a solid stylet is utilized as an introducer to properly position the flexible catheter within the ventricle.

Since cerebrospinal fluid within the brain ventricles is normally maintained under pressure, proper placement of a distal end of the ventricular catheter is indicated when the cerebrospinal fluid flows through the catheter inlet apertures and is presented at a catheter proximal end. A solid stylet, however, tends to occlude the internal fluid flow passageway through the catheter, thereby requiring the stylet to be withdrawn from the catheter in order to determine whether the distal end thereof is properly positioned. If the expected "flashback" of cerebrospinal fluid is not found at the proximal end of the catheter upon removal of the solid stylet, the stylet must be reinserted for further positioning of the ventricular catheter.

Accordingly, there has been a need for a novel stylet assembly useful for inserting a catheter into a brain ventricle and providing a cerebrospinal fluid flashback indicia of proper catheter positioning, without requiring withdrawal of the stylet assembly from the ventricular catheter. Such a stylet assembly should be of simplified construction utilizing materials which are easily sterilizable and compatible for biomedical usage. Further, there exists a need for a stylet assembly for inserting a catheter into a body cavity and providing a flashback indicia of catheter positioning, which permits the surgeon to readily occlude the fluid passageway when proper catheter positioning is indicated, in order to minimize and control the flow of fluid from the body cavity through the catheter. The present invention fulfills these needs and provides other related advantages.

SUMMARY OF THE INVENTION

The present invention resides in an improved closed end hollow stylet assembly designed primarily for inserting a catheter into a brain ventricle and providing a cerebrospinal fluid flashback indicia of proper catheter positioning. The stylet assembly comprises, generally, an elongated hollow stylet having an open distal end and a closed proximal end, means for permitting the cerebrospinal fluid to enter into the stylet, and a hub surrounding a portion of the stylet adjacent to the distal end.

In a preferred form of the invention, the stylet is generally cylindrical and is formed of a rigid material. An internal fluid passageway extends the length of the stylet for channeling cerebrospinal fluid from an inlet aperture adjacent to the proximal end of the stylet, to the open distal end. The proximal end of the stylet is rounded to prevent puncturing of the catheter when the stylet assembly is utilized to insert the catheter into the brain ventricle.

The means for permitting the cerebrospinal fluid to enter into the stylet comprises a relatively large, single lateral aperture through a wall of the stylet adjacent to the proximal end of the stylet. This relatively large lateral aperture is configured to underlie a plurality of catheter inlet apertures. In this regard, the lateral aperture has a width generally corresponding with the diameter of the internal fluid passageway.

The hub is preferably constructed of an elastomeric material and is configured to permit the flow of cerebrospinal fluid through the open distal end of the stylet. The elastomeric hub provides means for selectively manually occluding the open distal end of the stylet to prevent the flow of cerebrospinal fluid therethrough when flashback occurs. A distal end of the elastomeric hub includes a recess, and the open distal end of the stylet is generally flush with a bottom of the recess.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
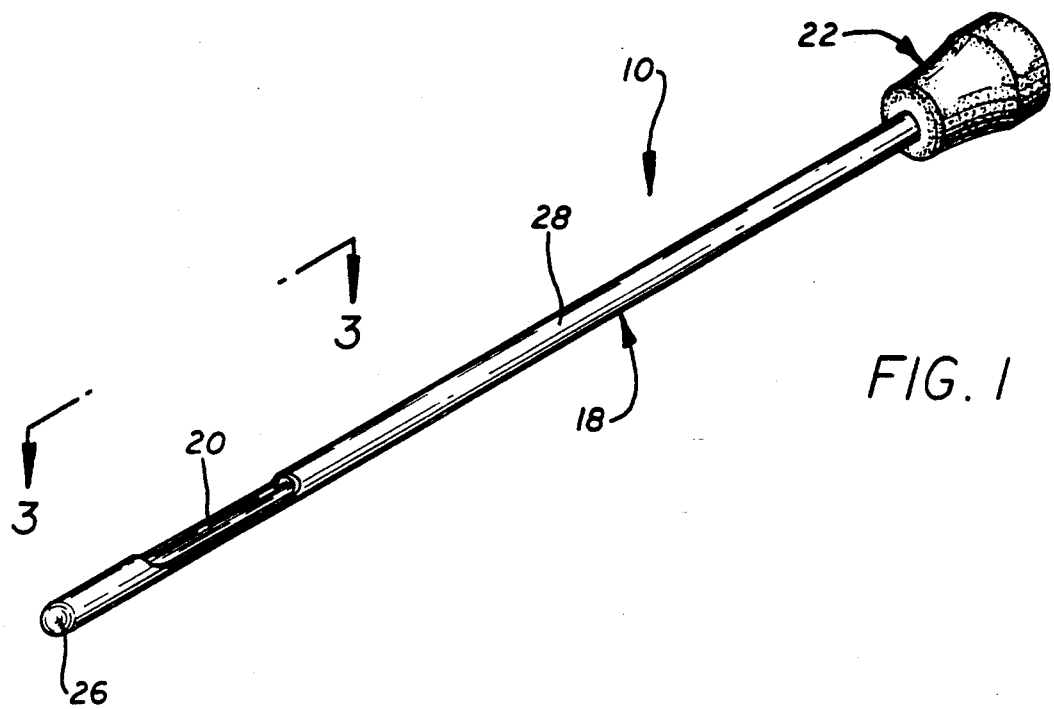
FIG. 1 is a perspective view of a closed end hollow stylet assembly embodying the invention.
Figure 2:
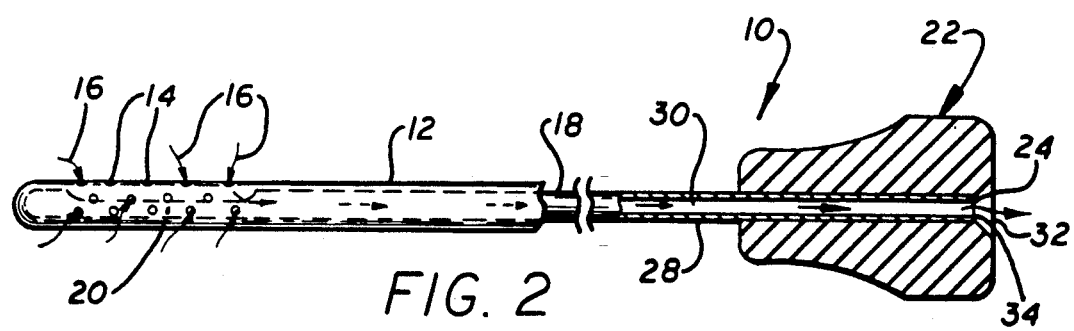
FIG. 2 is a partially sectional elevational view of the stylet assembly illustrated in FIG. 1, shown with a ventricular catheter enveloping a proximal end of the stylet assembly, and illustrating the configuration of a hub about a distal end of the stylet.
Figure 3:
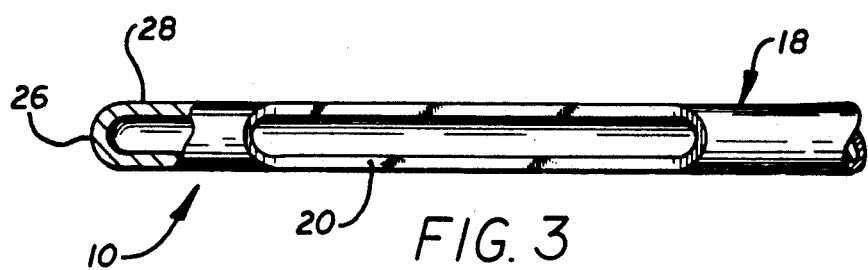
FIG. 3 is an enlarged fragmented top plan view of the stylet assembly taken generally in the direction of line 3—3 of FIG. 1, illustrating a relatively large aperture adjacent to a proximal end of the stylet, wherein the proximal end of the stylet is shown in cross section for illustrative purposes.

As shown in the drawings for purposes of illustration, the present invention is concerned with an improved stylet assembly, generally designated in the accompanying drawings by the reference number 10. The improved stylet assembly 10 is intended for use in inserting a ventricular catheter 12 into a brain ventricle and providing a cerebrospinal fluid flashback indicia of proper catheter positioning. As shown in FIG. 2, the ventricular catheter 12 is typically constructed of a flexible elastomeric material, such as a silicone elastomer, which has shown acceptable levels of tissue reaction. The catheter 12 is very flexible to minimize tissue irritation and reaction when implanted, and includes a plurality of inlet apertures 14 adjacent to its proximal end. When positioned within a brain ventricle, cerebrospinal fluid enters into the catheter 12 through the apertures 14 as indicated by the arrows 16, and is drained away through the catheter to another portion of the body.

In accordance with the present invention, the stylet assembly 10 comprises, generally, an elongated, generally cylindrical, rigid hollow stylet 18 configured for insertion into the ventricular catheter 12, a relatively large lateral aperture 20 through a wall of the stylet, and a hub 22 surrounding a portion of the stylet adjacent to a distal end thereof. The stylet 18 includes an open distal end 24 and a rounded, blunt closed proximal end 26. The body of the stylet 18 is defined by a 19 gauge stainless steel wall 28 which defines an internal fluid passageway 30 which extends the length of the stylet 18. The proximal end 26 of the stylet 18 is rounded to prevent puncturing of the catheter 12 when the catheter is inserted into the brain ventricle.

The lateral aperture 20 provides means generally adjacent to the proximal end of the stylet 18, for permitting the cerebrospinal fluid to enter into the internal fluid passageway 30, whereupon the fluid can freely travel through the stylet to the distal end 24. As shown, a relatively large, single aperture is provided in the wall 28, and is configured to underlie a plurality of the inlet apertures 14 of the ventricular catheter 12 (see FIG. 2). The aperture 20 preferably has a width generally corresponding with the diameter of the internal fluid passageway 30. The particular illustrated configuration of the aperture 20 maximizes the inlet opening through the stylet 18 to the internal fluid passageway 30, yet retains the structural integrity of the stylet for supporting the proximal end 26 thereof.

The hub 22 is preferably manufactured of a silicone elastomer with barium sulfate, and is configured to be easily grasped by a surgeon utilizing the stylet assembly 10. The hub 22 surrounds a portion of the stylet 18 adjacent to the distal end 24, and is configured to permit the flow of cerebrospinal fluid through the open distal end of the stylet. The hub 22 further provides means for selectively manually occluding the open distal end 24 of the stylet 18, to prevent the flow of cerebrospinal fluid therethrough.

More particularly, a distal end of the elastomeric hub 22 includes a recess 32. The open distal end 24 of the stylet 18 is positioned generally flush with a bottom 34 of the recess 32. This particular configuration of the distal end of the hub 22 permits the surgeon to simply place a finger over the recess 32 to stop the flow of cerebrospinal fluid through the stylet assembly 10 after proper catheter positioning has been achieved.

In use, the stylet assembly 10 is normally handled by the hub 22 when placed within and when withdrawn from the ventricular catheter 12. The stylet 18 is configured to be placed within the ventricular catheter 12 fully so that the proximal end 26 engages and pushes upon a proximal end of the catheter 12. When so inserted, the stylet assembly 10 is utilized to place the ventricular catheter 12 through a burr hole in the skull into a brain ventricle. The cerebrospinal fluid under pressure will flow through the inlet apertures 14 of the catheter 12, through the lateral aperture 20 into the internal fluid passageway 30 of the stylet 18, to the distal end 24 when properly positioned. This provides a flashback indicia of proper catheter placement within the brain ventricle. Upon achieving proper positioning of the catheter, the surgeon may occlude the fluid passageway through the stylet assembly 10 by placing a finger over the recess 32 provided in the hub 22, and withdraw the stylet 18 from the catheter 12.

From the foregoing it is to be appreciated that the improved stylet assembly 10 of the present invention can be easily manufactured of sterilizable materials compatible for use in biomedical applications. The stylet assembly 10 facilitates proper positioning of a catheter 12 within a brain ventricle by facilitating the flow of cerebrospinal fluid through the catheter 12 without requiring removal of the stylet assembly 10 therefrom.

Although a particular embodiment of the invention has been described in detail for purposes of illustration, various modifications may be made without departing from the spirit and scope of the invention. Accordingly, the invention is not to be limited, except as by the appended claims.

We claim:

1. A stylet assembly for placing a catheter into a brain ventricle for draining cerebrospinal fluid, the stylet assembly comprising:
   an elongated, generally cylindrical hollow stylet having an open distal end, a closed proximal end, and an internal fluid passageway extending the length of the stylet;
   means generally adjacent to the proximal end of the stylet, for permitting the cerebrospinal fluid to enter into the internal fluid passageway, including a single aperture in a wall of the stylet configured to underlie a plurality of catheter inlet apertures; and
   a hub surrounding a portion of the stylet adjacent to the distal end of the stylet, the hub being configured to permit the flow of cerebrospinal fluid through the open distal end of the stylet, and providing means for selectively manually occluding the open distal end of the stylet to prevent the flow of cerebrospinal fluid therethrough.

2. A stylet assembly as set forth in claim 1, wherein the proximal end of the stylet is rounded to prevent puncturing of the catheter when being inserted into the brain ventricle.

3. A stylet assembly as set forth in claim 1, wherein the aperture in the wall of the stylet has a width generally corresponding with the diameter of the internal fluid passageway.

4. A stylet assembly as set forth in claim 1, wherein a distal end of the hub includes a recess, and the open distal end of the stylet is generally flush with a bottom of the recess.

5. A stylet assembly for inserting a catheter into a body cavity and providing a flashback indicia of catheter positioning, the stylet assembly comprising:
   an elongated, generally cylindrical, rigid hollow stylet having an open distal end, a rounded blunt, proximal end, and an internal fluid passageway extending the length of the stylet;

a relatively large lateral aperture adjacent to the proximal end of the stylet, for permitting fluid flow into the stylet internal fluid passageway; and a hub surrounding a portion of the stylet adjacent to the distal end of the stylet, the hub being constructed of an elastomeric material configured to permit the flow of fluid through the open distal end of the stylet, and providing means for selectively manually occluding the open distal end of the stylet to prevent the flow of fluid therethrough.

6. A stylet assembly as set forth in claim 5, wherein a distal end of the elastomeric hub includes a recess, and the open distal end of the stylet is generally flush with a bottom of the recess.

7. A stylet assembly as set forth in claim 5, wherein the relatively large aperture is configured to underlie a plurality of catheter inlet apertures.

8. A stylet assembly as set forth in claim 7, wherein the relatively large aperture has a width generally corresponding with the diameter of the internal fluid passageway.

9. A stylet assembly for inserting a catheter into a brain ventricle and providing a cerebrospinal fluid flashback indicia of proper catheter positioning, the stylet assembly comprising:

an elongated, generally cylindrical, rigid hollow stylet having an open distal end, a rounded blunt, closed proximal end, and an internal fluid passageway extending the length of the stylet;

a relatively large lateral, single aperture adjacent to the proximal end of the stylet, for permitting cerebrospinal fluid flow into the stylet internal fluid passageway, the aperture being configured to underlie a plurality of catheter inlet apertures and having a width generally corresponding with the diameter of the internal fluid passageway; and an elastomeric hub surrounding a portion of the stylet adjacent to the distal end of the stylet, the hub being configured to permit the flow of cerebrospinal fluid through the open distal end of the stylet, and providing means for selectively manually occluding the open distal end of the stylet to prevent the flow of cerebrospinal fluid therethrough, the elastomeric hub including a recess wherein the open distal end of the stylet is generally flush with a bottom of the recess.

10. A stylet assembly for inserting a catheter into a body cavity and providing a flashback indicia of catheter positioning, the stylet assembly comprising:

an elongated, generally cylindrical, rigid hollow stylet having an open distal end, a rounded blunt proximal end, and an internal fluid passageway extending the length of the stylet;

a relatively large lateral aperture adjacent to the proximal end of the stylet having a width generally corresponding with the diameter of the internal fluid passageway and being configured to underlie a plurality of catheter inlet apertures, for permitting fluid flow into the stylet internal fluid passageway; and a hub surrounding a portion of the stylet adjacent to the distal end of the stylet.

11. A stylet assembly as set forth in claim 10, wherein the hub is constructed of an elastomeric material and is configured to permit the flow of fluid through the open distal end of the stylet, wherein the elastomeric hub provides means for selectively manually occluding the open distal end of the stylet to prevent the flow of fluid therethrough.

12. A stylet assembly as set forth in claim 11, wherein a distal end of the elastomeric hub includes a recess, and the open distal end of the stylet is generally flush with a bottom of the recess.

* * * * *